US006213126B1

(12) United States Patent
LaFontaine et al.

(10) Patent No.: US 6,213,126 B1
(45) Date of Patent: Apr. 10, 2001

(54) PERCUTANEOUS ARTERY TO ARTERY BYPASS USING HEART TISSUE AS A PORTION OF A BYPASS CONDUIT

(75) Inventors: Daniel M. LaFontaine, Plymouth; Thomas R. Hektner, Medina; Kent D. Harrison, Maple Grove, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 08/878,933

(22) Filed: Jun. 19, 1997

(51) Int. Cl.$^7$ .................................................. A61B 19/00

(52) U.S. Cl. ............................................................ 128/898

(58) Field of Search .................... 128/898; 623/1, 623/21, 66, 11; 604/2, 4, 5, 96–103, 18, 49; 600/18, 201, 204; 606/49

(56) References Cited

U.S. PATENT DOCUMENTS

| Re. 35,352 | 10/1996 | Peters . |
|---|---|---|
| Re. 35,459 | 2/1997 | Junkman . |
| 3,667,069 | 6/1972 | Blackshear et al. . |
| 4,016,884 | 4/1977 | Kwan-Gett . |
| 4,165,747 | 8/1979 | Bermant . |
| 4,173,981 | 11/1979 | Mortensen . |
| 4,190,909 | 3/1980 | Ablaza . |
| 4,230,096 | 10/1980 | Zeff et al. . |
| 4,546,499 | 10/1985 | Possis et al. . |
| 4,562,597 | 1/1986 | Possis et al. . |
| 4,566,453 | 1/1986 | Kumano et al. . |
| 4,601,718 | 7/1986 | Possis et al. . |
| 4,610,661 | 9/1986 | Possis et al. . |
| 4,667,673 | 5/1987 | Li . |
| 4,690,684 | 9/1987 | McGreevy et al. . |
| 4,710,192 | 12/1987 | Liotta et al. . |
| 4,721,109 | 1/1988 | Healey . |
| 4,790,819 | 12/1988 | Li et al. . |
| 4,803,984 | 2/1989 | Narayanan et al. . |
| 4,808,163 | 2/1989 | Laub . |
| 4,819,640 | 4/1989 | Narayanan et al. . |
| 4,827,931 | 5/1989 | Longmore . |
| 4,907,591 | 3/1990 | Vasconellos et al. . |

(List continued on next page.)

FOREIGN PATENT DOCUMENTS

| 0 769 272 A1 | 4/1997 | (EP) . |
|---|---|---|
| 97-281410 | 7/1997 | (JP) . |
| 1600708 | 12/1995 | (RU) . |

(List continued on next page.)

OTHER PUBLICATIONS

"The Current Status of Lasers in the Treatment of Cardiovascular Disease" by Jeffrey M. Isner and Richard H. Clarke, IEEE, vol. QE–20, No. 12, Dec. 1984, pp. 1406–1420.

"The Possibility of Myocardial Revascularization by Creation of a Left Ventriculocoronary Artery Fistula", by Ian Munro and Peter Alllen, M.D., *Journal of Thoracic and Cardiovascular Surgery*, vol. 58, No. 1, Jul. 1969, pp. 25–32.

Primary Examiner—Dinh X. Nguyen
Assistant Examiner—Kelly O'Hara
(74) Attorney, Agent, or Firm—Westman, Champlin & Kelly, P.A.

(57) ABSTRACT

A restriction in a restricted vessel lying closely proximate the heart is bypassed. An aperture is formed in a supply vessel suitable for providing a blood supply. An aperture is formed in the restricted vessel distal of the restriction. Heart tissue is removed from the surface of the heart to form a channel in the heart tissue between the aperture in the supply vessel and the aperture in the restricted vessel distal of the restriction. The channel is covered to form a conduit to conduct blood from the supply vessel to the restricted vessel distal of the restriction.

22 Claims, 11 Drawing Sheets

U.S. PATENT DOCUMENTS

| | | |
|---|---|---|
| 4,911,164 | 3/1990 | Roth . |
| 4,995,857 | 2/1991 | Arnold . |
| 5,011,469 | 4/1991 | Buckberg et al. . |
| 5,037,428 | 8/1991 | Picha et al. . |
| 5,047,039 | 9/1991 | Avant et al. . |
| 5,053,041 | 10/1991 | Ansari et al. . |
| 5,053,043 | 10/1991 | Gottesman et al. . |
| 5,061,245 | 10/1991 | Waldvogel . |
| 5,067,958 | 11/1991 | Sandhaus . |
| 5,080,663 | 1/1992 | Mills et al. . |
| 5,080,664 | 1/1992 | Jain . |
| 5,104,402 | 4/1992 | Melbin . |
| 5,144,961 | 9/1992 | Chen et al. . |
| 5,222,962 | 6/1993 | Burkhart . |
| 5,222,963 | 6/1993 | Brinkerhoff et al. . |
| 5,222,971 | 6/1993 | Willard et al. . |
| 5,234,445 | 8/1993 | Walker et al. . |
| 5,254,113 | 10/1993 | Wilk . |
| 5,281,236 | 1/1994 | Bagnato et al. . |
| 5,282,810 | 2/1994 | Allen et al. . |
| 5,287,861 | 2/1994 | Wilk . |
| 5,308,320 | 5/1994 | Safar et al. . |
| 5,314,436 | 5/1994 | Wilk . |
| 5,314,472 | 5/1994 | Fontaine . |
| 5,323,789 | 6/1994 | Berggren et al. . |
| 5,330,486 | 7/1994 | Wilk . |
| 5,370,683 | 12/1994 | Fontaine . |
| 5,382,257 | 1/1995 | Lewis et al. . |
| 5,383,854 | 1/1995 | Safar et al. . |
| 5,383,928 | 1/1995 | Scott et al. . |
| 5,397,345 | 3/1995 | Lazarus . |
| 5,403,333 | 4/1995 | Kaster et al. . |
| 5,409,019 | 4/1995 | Wilk . |
| 5,425,705 | 6/1995 | Evard et al. . |
| 5,425,739 | 6/1995 | Jessen . |
| 5,429,144 | 7/1995 | Wilk . |
| 5,433,700 | 7/1995 | Peters . |
| 5,437,684 | 8/1995 | Calabrese et al. . |
| 5,441,507 | 8/1995 | Wilk . |
| 5,443,497 | 8/1995 | Venbrux . |
| 5,447,512 | 9/1995 | Wilson et al. . |
| 5,449,372 | 9/1995 | Schmaltz et al. . |
| 5,452,733 | 9/1995 | Sterman et al. . |
| 5,456,714 | 10/1995 | Owen . |
| 5,472,404 | 12/1995 | Volgushev . |
| 5,501,698 | 3/1996 | Roth et al. . |
| 5,522,884 | 6/1996 | Wright . |
| 5,527,319 | 6/1996 | Green et al. . |
| 5,527,324 | 6/1996 | Krantz et al. . |
| 5,536,251 | 7/1996 | Evard et al. . |
| 5,540,677 | 7/1996 | Sinofsky . |
| 5,540,701 | 7/1996 | Sharkey et al. . |
| 5,545,171 | 8/1996 | Sharkey et al. . |
| 5,554,162 | 9/1996 | DeLange . |
| 5,556,414 | 9/1996 | Turi . |
| 5,556,428 | 9/1996 | Shah . |
| 5,562,728 | 10/1996 | Lazarus et al. . |
| 5,569,272 | 10/1996 | Reed et al. . |
| 5,569,274 | 10/1996 | Rapacki et al. . |
| 5,571,090 | 11/1996 | Sherts . |
| 5,571,215 | 11/1996 | Sterman et al. . |
| 5,584,803 | 12/1996 | Stevens et al. . |
| 5,588,949 | 12/1996 | Taylor et al. . |
| 5,591,179 | 1/1997 | Edelstein . |
| 5,591,212 | 1/1997 | Keimel . |
| 5,593,424 | 1/1997 | Northrup, III .................. 606/232 |
| 5,601,576 | 2/1997 | Garrison . |
| 5,601,581 | 2/1997 | Fogarty et al. . |
| 5,609,598 | 3/1997 | Laufer et al. . |
| 5,613,937 | 3/1997 | Garrison et al. . |
| 5,618,270 | 4/1997 | Orejola . |
| 5,643,292 | 7/1997 | Hart . |
| 5,653,744 | 8/1997 | Khouri . |
| 5,655,548 | 8/1997 | Nelson et al. . |
| 5,662,124 | 9/1997 | Wilk . |
| 5,662,711 | 9/1997 | Douglas . |
| 5,676,670 | 10/1997 | Kim . |
| 5,682,906 | 11/1997 | Sterrman et al. . |
| 5,685,857 | 11/1997 | Negus et al. . |
| 5,693,083 | 12/1997 | Baker et al. . |
| 5,702,368 | 12/1997 | Stevens et al. . |
| 5,702,412 | 12/1997 | Popov et al. .................. 606/159 |
| 5,715,832 | 2/1998 | Koblish et al. . |
| 5,716,367 | 2/1998 | Koike et al. . |
| 5,718,725 | 2/1998 | Sterman et al. . |
| 5,722,426 | 3/1998 | Kolff . |
| 5,725,537 | 3/1998 | Green et al. . |
| 5,727,569 | 3/1998 | Benetti et al. . |
| 5,728,151 | 3/1998 | Garrison et al. . |
| 5,735,290 | 4/1998 | Sterman et al. . |
| 5,738,649 | 4/1998 | Macoviak . |
| 5,738,652 | 4/1998 | Boyd et al. . |
| 5,749,892 | 5/1998 | Vierra et al. . |
| 5,752,526 | 5/1998 | Cosgrove . |
| 5,755,682 | 5/1998 | Knudson et al. . |
| 5,755,687 | 5/1998 | Donlon . |
| 5,755,778 | 5/1998 | Kleshinski . |
| 5,758,663 | 6/1998 | Wilk et al. . |
| 5,766,151 | 6/1998 | Valley et al. . |
| 5,769,812 | 6/1998 | Stevens et al. . |
| 5,792,094 | 8/1998 | Stevens et al. . |
| 5,795,325 | 8/1998 | Valley et al. . |
| 5,797,920 | 8/1998 | Kim . |
| 5,797,933 | 8/1998 | Snow et al. . |
| 5,799,661 | 9/1998 | Boyd et al. . |
| 5,800,450 | 9/1998 | Lary et al. . |
| 5,800,522 | 9/1998 | Campbell et al. . |
| 5,836,311 | 11/1998 | Borst et al. . |
| 5,849,036 | 12/1998 | Zarate . |
| 5,855,210 | 1/1999 | Sterman et al. . |
| 5,855,614 | 1/1999 | Stevens et al. . |
| 5,868,770 | 2/1999 | Rygaard . |
| 5,906,607 | 5/1999 | Taylor et al. .................. 606/1 |
| 5,916,193 | 6/1999 | Stevens et al. .................. 604/53 |

FOREIGN PATENT DOCUMENTS

| | | |
|---|---|---|
| 308752 | 7/1971 | (SU) . |
| 388738 | 9/1971 | (SU) . |
| 891076 | 12/1981 | (SU) . |
| 1822750 A1 | 7/1982 | (SU) . |
| WO 95/08364 | 3/1995 | (WO) . |
| WO 95/10218 | 4/1995 | (WO) . |
| WO 95/15192 | 6/1995 | (WO) . |
| WO 95/16476 | 6/1995 | (WO) . |
| WO 96/10375 | 4/1996 | (WO) . |
| WO 96/17644 | 6/1996 | (WO) . |
| WO 96/25886 | 8/1996 | (WO) . |
| WO 96/30072 | 10/1996 | (WO) . |
| WO 96/30073 | 10/1996 | (WO) . |
| WO 96/32882 | 10/1996 | (WO) . |
| WO 97/12555 | 4/1997 | (WO) . |
| WO 97/13463 | 4/1997 | (WO) . |
| WO 97/13468 | 4/1997 | (WO) . |
| WO 97/13471 | 4/1997 | (WO) . |
| WO 97/26939 | 7/1997 | (WO) . |
| WO 97/37984 | 10/1997 | (WO) . |
| WO 97/40751 | 11/1997 | (WO) . |
| WO 98/06356 | 2/1998 | (WO) . |
| WO 98/07399 | 2/1998 | (WO) . |
| WO 98/10714 | 3/1998 | (WO) . |
| WO 98/15237 | 4/1998 | (WO) . |

| | | |
|---|---|---|
| WO 98/16161 | 4/1998 | (WO) . |
| WO 98/16174 | 4/1998 | (WO) . |
| WO 98/17182 | 4/1998 | (WO) . |
| WO 98/17187 | 4/1998 | (WO) . |
| WO 98/19607 | 5/1998 | (WO) . |
| WO 98/19634 | 5/1998 | (WO) . |
| WO 98/19636 | 5/1998 | (WO) . |
| WO 98/31302 | 7/1998 | (WO) . |
| WO 98/32380 | 7/1998 | (WO) . |
| WO 98/35626 | 8/1998 | (WO) . |
| WO 98/37814 | 9/1998 | (WO) . |
| WO 98/51223 | 11/1998 | (WO) . |
| WO 98/52474 | 11/1998 | (WO) . |
| WO 98/52475 | 11/1998 | (WO) . |
| WO 98/57590 | 12/1998 | (WO) . |
| WO 98/57591 | 12/1998 | (WO) . |
| WO 98/57592 | 12/1998 | (WO) . |
| WO 99/04836 | 2/1999 | (WO) . |
| WO 99/04845 | 2/1999 | (WO) . |
| WO 99/21490 | 5/1999 | (WO) . |
| WO 99/24102 | 5/1999 | (WO) . |

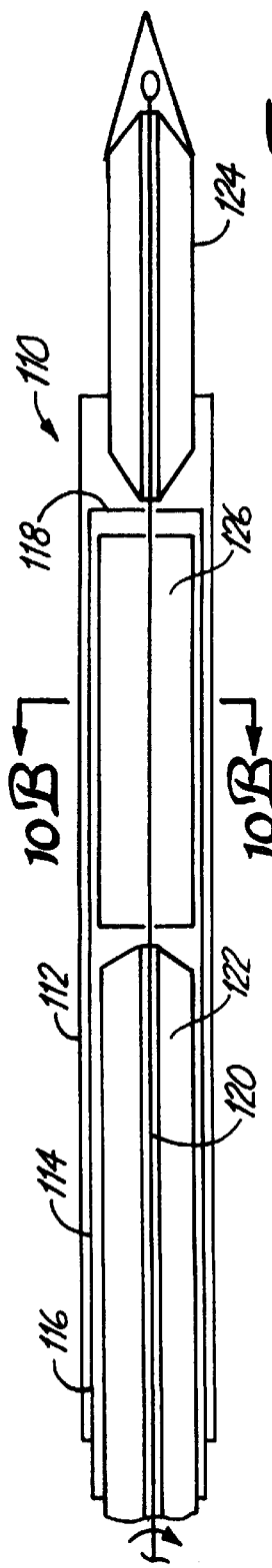
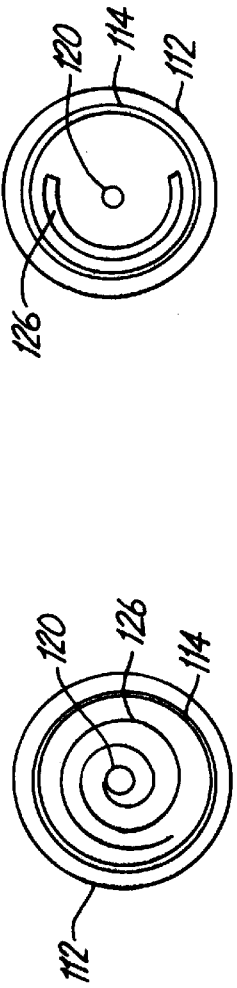
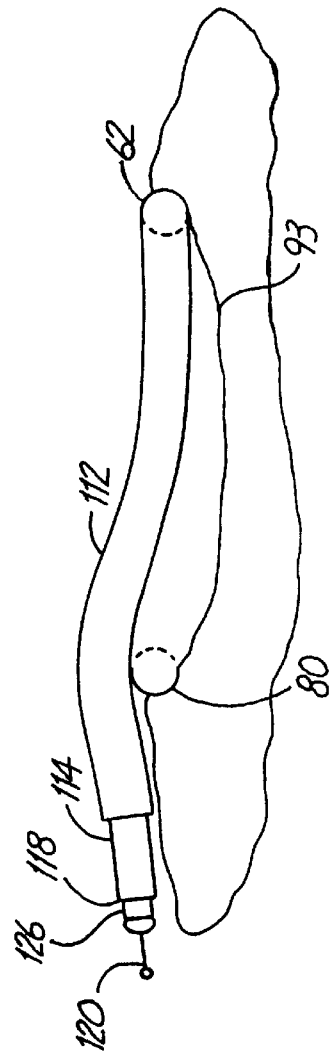
Fig. 10A
Fig. 10B
Fig. 10C
Fig. 10D

PERCUTANEOUS ARTERY TO ARTERY BYPASS USING HEART TISSUE AS A PORTION OF A BYPASS CONDUIT

INCORPORATION BY REFERENCE

The following U.S. patent applications are hereby fully incorporated:

U.S. patent application Ser. No. 08/878,804, entitled PERCUTANEOUS CHAMBER-TO-ARTERY BYPASS, filed on even date herewith and assigned to the same assignee as the present application;

U.S. patent application Ser. No. 09/088,496, entitled PERCUTANEOUS CORONARY ARTERY BYPASS THROUGH A VENOUS VESSEL, filed on even date herewith and assigned to the same assignee as the present application;

U.S. patent application Ser. No. 08/813,038, entitled SYSTEM AND METHOD FOR PERCUTANEOUS CORONARY ARTERY BYPASS, filed on Mar. 6, 1997, issued Feb. 22, 2000 as U.S. Pat. No. 6,026,814, and assigned to the same assignee as the present application;

U.S. patent application Ser. No. 08/813,040, entitled PERCUTANEOUS BYPASS WITH BRANCHING VESSEL, filed on Mar. 6, 1997, issued Mar. 14, 2000 as U.S. Pat. No. 6,035,856 and assigned to the same assignee as the present application; and U.S. patent application Ser. No. 08/812,879, entitled PERCUTANEOUS BYPASS BY TUNNELING THROUGH VESSEL WALL, filed on Mar. 6, 1997 and assigned to the same assignee as the present application.

BACKGROUND OF THE INVENTION

The present invention generally deals with vascular bypass methods. More specifically, the present invention deals with systems for performing percutaneous coronary artery bypass procedures.

Coronary arteries can become partially restricted (stenotic) or completely clogged (occluded) with plaque, thrombus, or the like. This reduces the efficiency of the heart, and can ultimately lead to a heart attack. Thus, a number of different systems and methods have been developed for treating stenotic or occluded coronary arteries.

Two methods which have been developed to treat occlusions and stenosis include balloon angioplasty and pharmacological treatment. However, where the occlusion is quite hard, it can be quite difficult, if not impossible, to cross the occlusion with an angioplasty device. In addition, some coronary stenosis are too diffuse to treat effectively with balloon angioplasty. Unfortunately, such occlusions are not readily susceptible to dissolution with chemicals either. In the past, patients with these types of occlusions have been candidates for open heart surgery to bypass the restrictions.

However, open heart surgery includes a myriad of disadvantages. Open heart surgery typically includes a great deal of postoperative pain. The pain is normally encountered because conventional open heart surgery requires that the sternum be cracked open, which is quite painful. Also, open heart surgery typically involves bypassing the occluded vessel, which, in turn, involves harvesting a vein from another part of the body for use as the bypass graft. One common source for the bypass graft is the saphenous vein which is removed from the leg. Harvesting the saphenous vein requires the surgeon to cut and peel the skin back from an area of the leg which is approximately 18 inches long and which extends upward to the groin area. This can be very traumatic and painful. Also, the internal mammary artery (IMA) has also been used as a vein graft in performing a bypass. However, the IMA is typically best suited for use as a left anterior descending (LAD) graft and is commonly saved for that purpose. Further, open heart surgery requires quite a lengthy recovery period which involves an increased hospital stay, and, consequently, greater expense.

Other than the pain and more lengthy hospital stay, open heart surgery involves other disadvantages as well. For example, during open heart surgery, it is common to cool the heart to a point where it stops. The blood from the remainder of the vasculature is then pumped through a pulmonary and cardiac bypass system. Any time the heart is stopped, there is a danger of encountering difficulty in restarting the heart (which is typically accomplished by warming the heart and massaging it). Further, even if the heart is restarted, it sometimes does not return to a correct rhythm. Also, open heart surgery can require the use of a device known as a left ventricular assist device (LVAD) to supplementarily pump blood to relieve the burden on the heart. This allows the heart to heal.

A significant reason that the heart is typically stopped during open heart surgery is that, if it were not stopped, the surgeon would be working in a dynamic environment. In such an environment, the target vessels and tissue to be treated are moving. Further, a system must be employed in such an environment to stop bleeding. Clinical studies indicate that, when blood flow is stopped using clamping devices and blood flow is diverted to a cardiac bypass system, a statistically significant instance of neurological problems caused by blood clotting results. The use of mechanical clamps to stop blood flow, and the use of a mechanical bypass system, results in an approximate six percent instance of neurological problems, such as stroke, memory failure, etc.

Given the difficulties of the techniques discussed above, another approach has been developed which does not require stoppage of the heart or an open chest during execution. This approach is to perform a bypass using a minimally invasive technique by entering the upper chest cavity, through a hole between ribs under visual observation. Such a technique is often referred to as minimally invasive direct coronary artery bypass (MIDCAB) (where the heart is not stopped) or heart port (where the heart is stopped). Such a system which is used to perform a bypass is disclosed in the Sterman et al. U.S. Pat. No. 5,452,733.

SUMMARY OF THE INVENTION

A restriction in a restricted vessel lying closely proximate the heart is bypassed. An aperture is formed in a supply vessel suitable for providing a blood supply. An aperture is formed in the restricted vessel distal of the restriction. Heart tissue is removed from the surface of the heart to form a channel in the heart tissue between the aperture in the supply vessel and the aperture in the restricted vessel distal of the restriction. The channel is covered to form a conduit to conduct blood from the supply vessel to the restricted vessel distal of the restriction.

BRIEF DESCRIPTION OF THE DRAWINGS

FIGS. 10A–10K illustrates a system for deploying a covering layer in accordance with one aspect of the present invention.

DETAILED DESCRIPTION OF THE PREFERRED EMBODIMENTS

Figure 1:
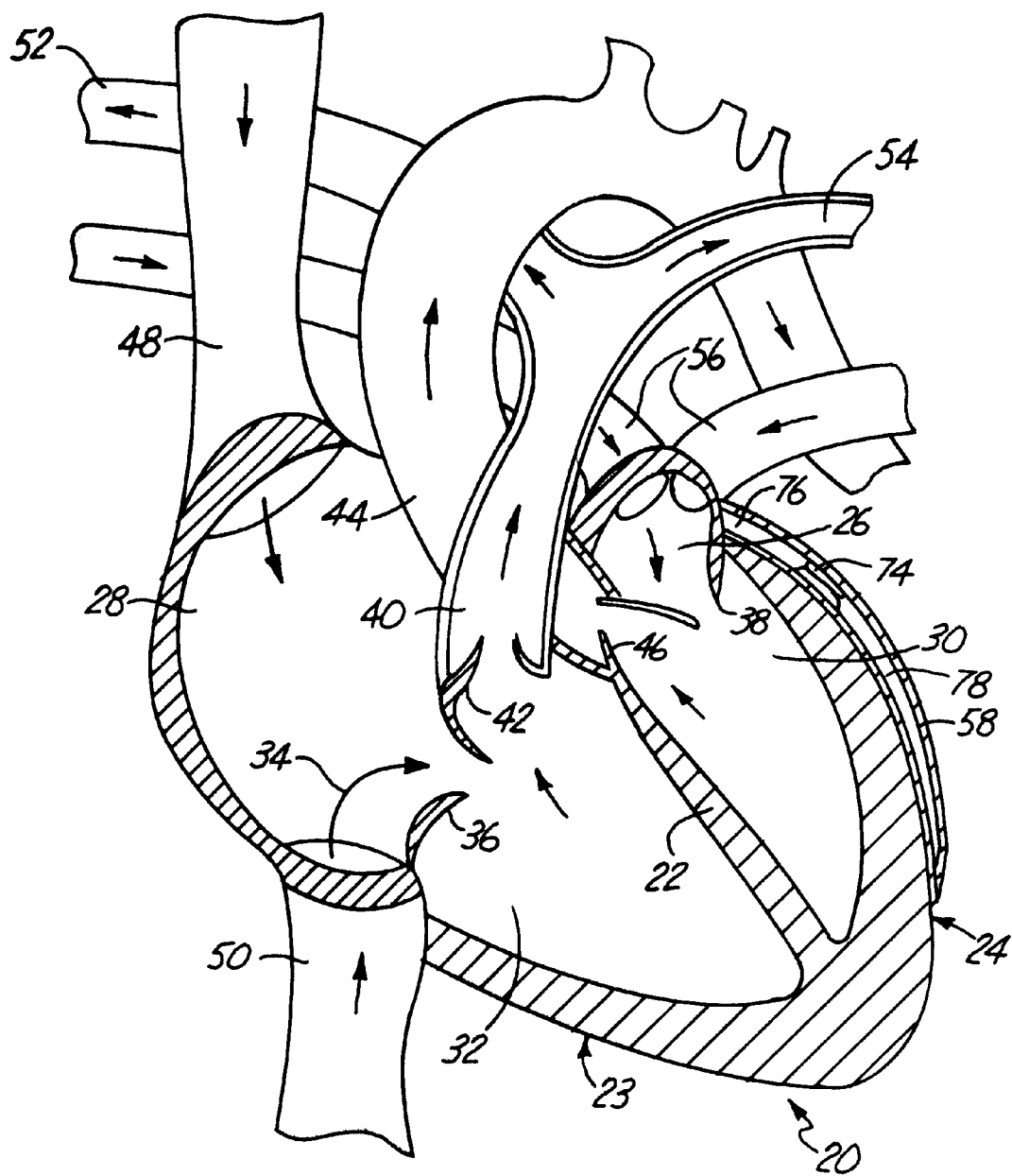
FIG. 1 illustrates a partial sectional view of a human heart and its associated proximate vascular system with a coronary artery having a restriction.

FIG. 1 illustrates a partially sectioned view of a human heart 20, and its associated vasculature. The heart 20 is subdivided by muscular septum 22 into two lateral halves, which are named respectively right 23 and left 24. A transverse constriction subdivides each half of the heart into two cavities, or chambers. The upper chambers consist of the left and right atria 26, 28 which collect blood. The lower chambers consist of the left and right ventricles 30, 32 which pump blood. The arrows 34 indicate the direction of blood flow through the heart.

The right atrium 28 communicates with the right ventricle 32 by the tricuspid valve 36. The left atrium 26 communicates with the left ventricle 30 by the mitral valve. The right ventricle 32 empties into the pulmonary artery 40 by way of the pulmonary valve 42. The left ventricle 30 empties into the aorta 44 by way of the aortic valve 46.

The circulation of the heart 20 consists of two components. First is the functional circulation of the heart 20, i.e., the blood flow through the heart 20 from which blood is pumped to the lungs and the body in general. Second is the coronary circulation, i.e., the actual blood supply to the structures and muscles of the heart 20 itself.

The functional circulation of the heart 20 pumps blood to the body in general, i.e., the systematic circulation, and to the lungs for oxygenation, i.e., the pulmonic and pulmonary circulation. The left side of the heart 24 supplies the systemic circulation. The right side 23 of the heart supplies the lungs with blood for oxygenation. Deoxygenated blood from the systematic circulation is returned to the heart 20 and is supplied to the right atrium 28 by the superior and inferior venae cavae 48, 50. The heart 20 pumps the deoxygenated blood into the lungs for oxygenation by way of the main pulmonary artery 40. The main pulmonary artery 40 separates into the right and left pulmonary arteries, 52, 54 which circulates to the right and left lungs, respectively. Oxygenated blood returns to the heart 20 at the left atrium 26 via four pulmonary veins 56 (of which two are shown). The blood then flows to the left ventricle 30 where it is pumped into the aorta 44, which supplies the body with oxygenated blood.

The functional circulation, however, does not supply blood to the heart muscle or structures. Therefore, functional circulation does not supply oxygen or nutrients to the heart 20 itself. The actual blood supply to the heart structure, i.e., the oxygen and nutrient supply, is provided by the coronary circulation of the heart, consisting of coronary arteries, indicated generally at 58, and cardiac veins. Coronary artery 58 can have a restriction 74. The coronary artery 58 includes a proximal arterial bed 76 between the aorta 44 and the restriction 74. Also, the coronary artery 58 includes a distal arterial bed 78 downstream from the restriction 74.

Figure 2:
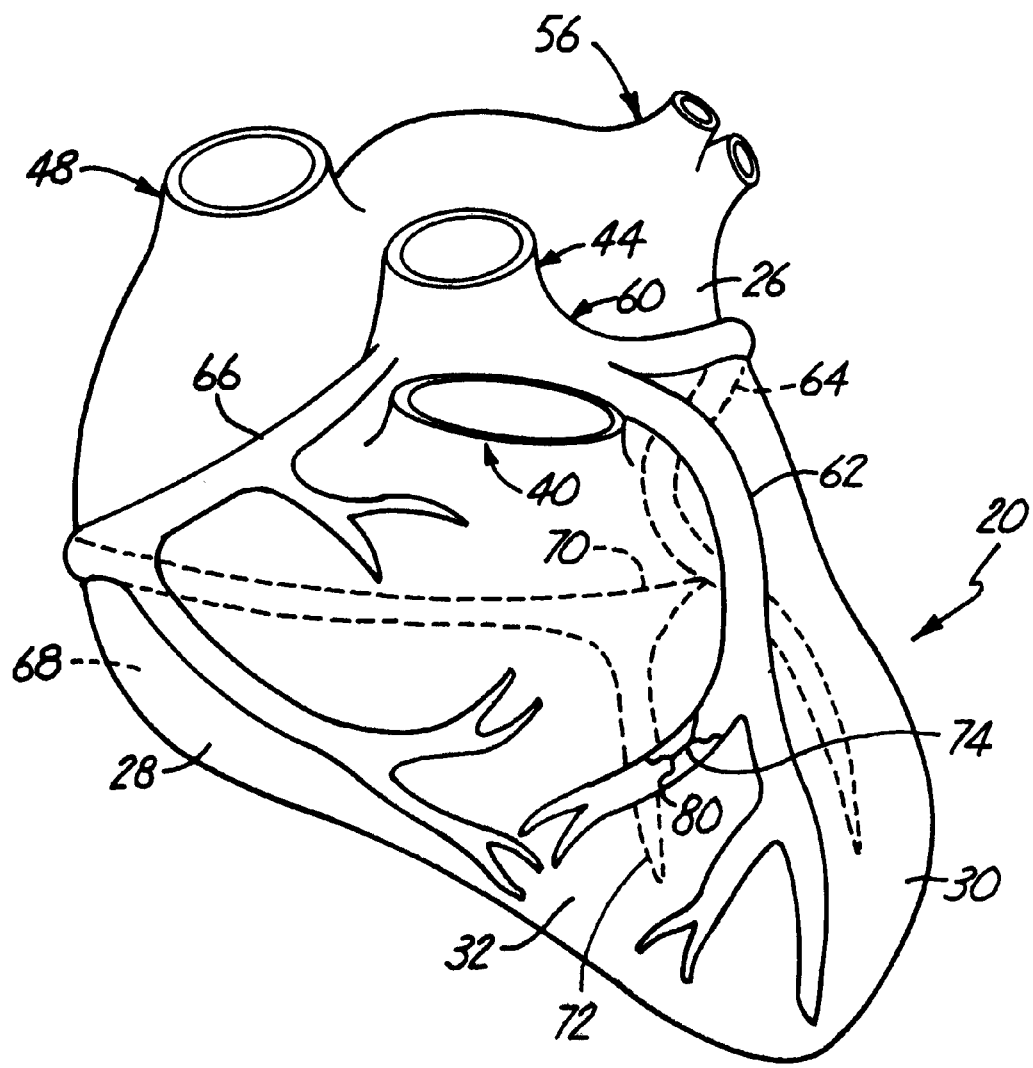
FIG. 2 illustrates a view of the heart of FIG. 1 with the major coronary arteries indicated thereon.

FIG. 2 shows the main coronary arteries of the heart 20. There are two main coronary arteries arising from the base of the aorta 44 and running along the heart 20 itself. The left main coronary artery 60 bifurcates into a left anterior descending branch 62 and the left circumflex branch 64. The left coronary artery 60 supplies the left atrium 26, gives branches to both ventricles 30, 32, and numerous small branches to the pulmonary artery 40. The right main coronary artery 66 runs along the posterior surface 68 of the heart 20 where it divides into a transverse branch 70 and a descending branch 72. The right coronary artery 66 supplies blood to the posterior aspect of the left ventricle 30. Both coronary arteries include a plurality of marginal branches, indicated only generally in the Figures. Coronary artery 58 is a generalized view of the arteries shown in FIG. 2, inasmuch as a restriction can occur in any coronary artery. However, the present description will proceed illustrating restriction 74 in a branch 80 of the left anterior descending branch 62 of left coronary artery 60.

The present invention bypasses restriction 74 by forming a channel or trench in the heart tissue between an unrestricted portion of an artery and a portion of branch 80 distal of restriction 74. The trench or channel is then covered by a covering layer to form a conduit between the supply vessel and the portion of branch 80 distal of restriction 74 to supply additional blood flow to the region of branch 80 distal of restriction 74.

Figure 3:
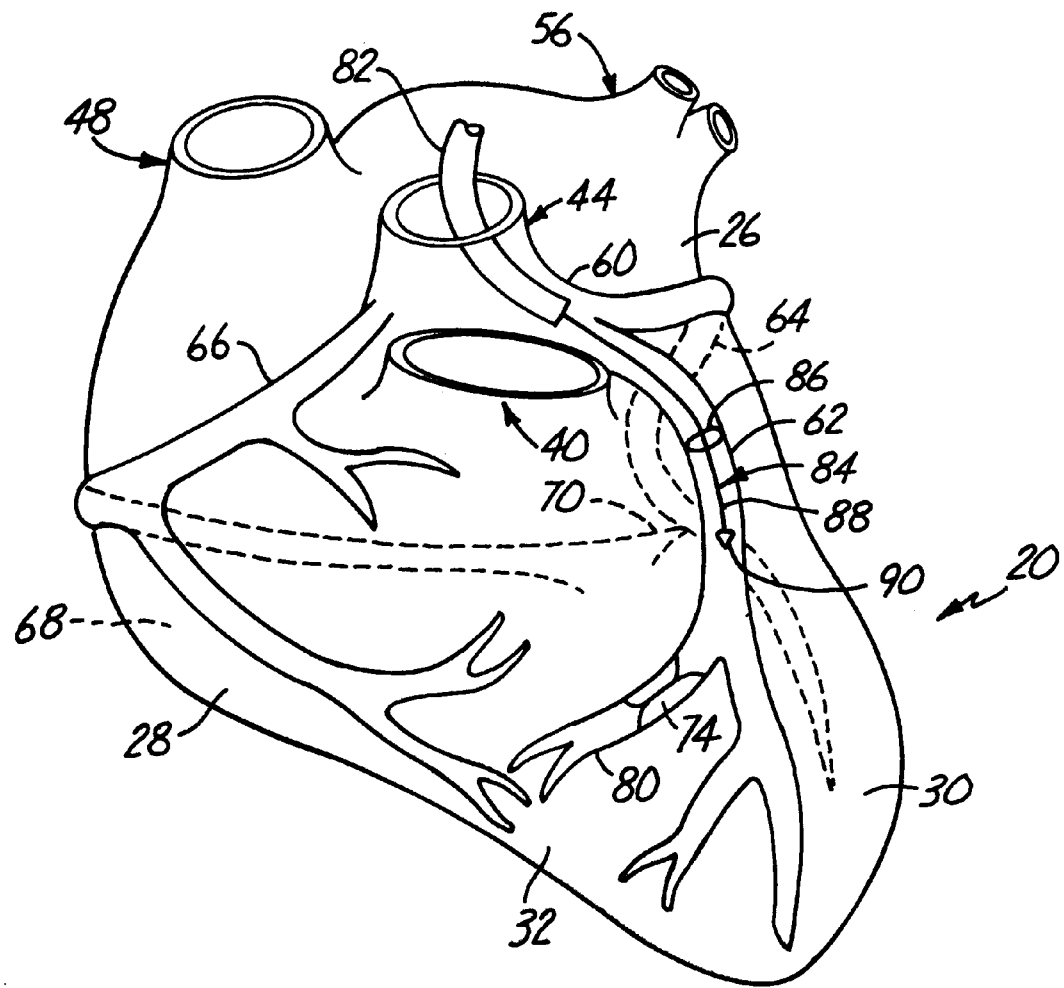
FIGS. 3–6 illustrate steps in performing a bypass in accordance with one embodiment of the present invention.

FIG. 3 illustrates a first step in performing a bypass in accordance with one preferred embodiment of the present invention. A conventional guide catheter 82 is first preferably advanced through the vasculature (preferably via a femoral artery) to aorta 44 where it is positioned with its distal end proximate the ostium of artery 62. Then, cutting device 84 is advanced through guide catheter 82 and out the distal end of guide catheter 82 to a region of vessel 62 proximal of restriction 74. In one preferred embodiment, cutting device 84 also includes a balloon catheter portion suitable for inflating a balloon 86. Balloon 86 is used for temporarily occluding vessel 62 during performance of the bypass. It should also be noted that the balloon catheter can be separate from cutting device 84.

Cutting device 84 is then used to pierce the wall of artery 62 proximal of restriction 74. Cutting device 84 can be any suitable cutting or debulking device which is suitable for forming a trench in heart tissue, such as a cutting catheter, a fully articulated cutting catheter, or any other suitable type of cutting or debulking device. It should also be noted, however, that cutting device 84 can be any suitable mechanical cutting device, or any suitable sort of energy device, such as a radio frequency (RF) ablation wire, or a laser, or other device. Cutting device 84 may preferably include a tubular or catheter portion 88 and a boring or cutting member 90. Boring or cutting member 90 can take any number of suitable forms, such as a rotatable member or a blade which can be used in piercing and boring through tissue. The cutting device is used to form a hole or aperture in the wall of vessel 62.

Figure 4:
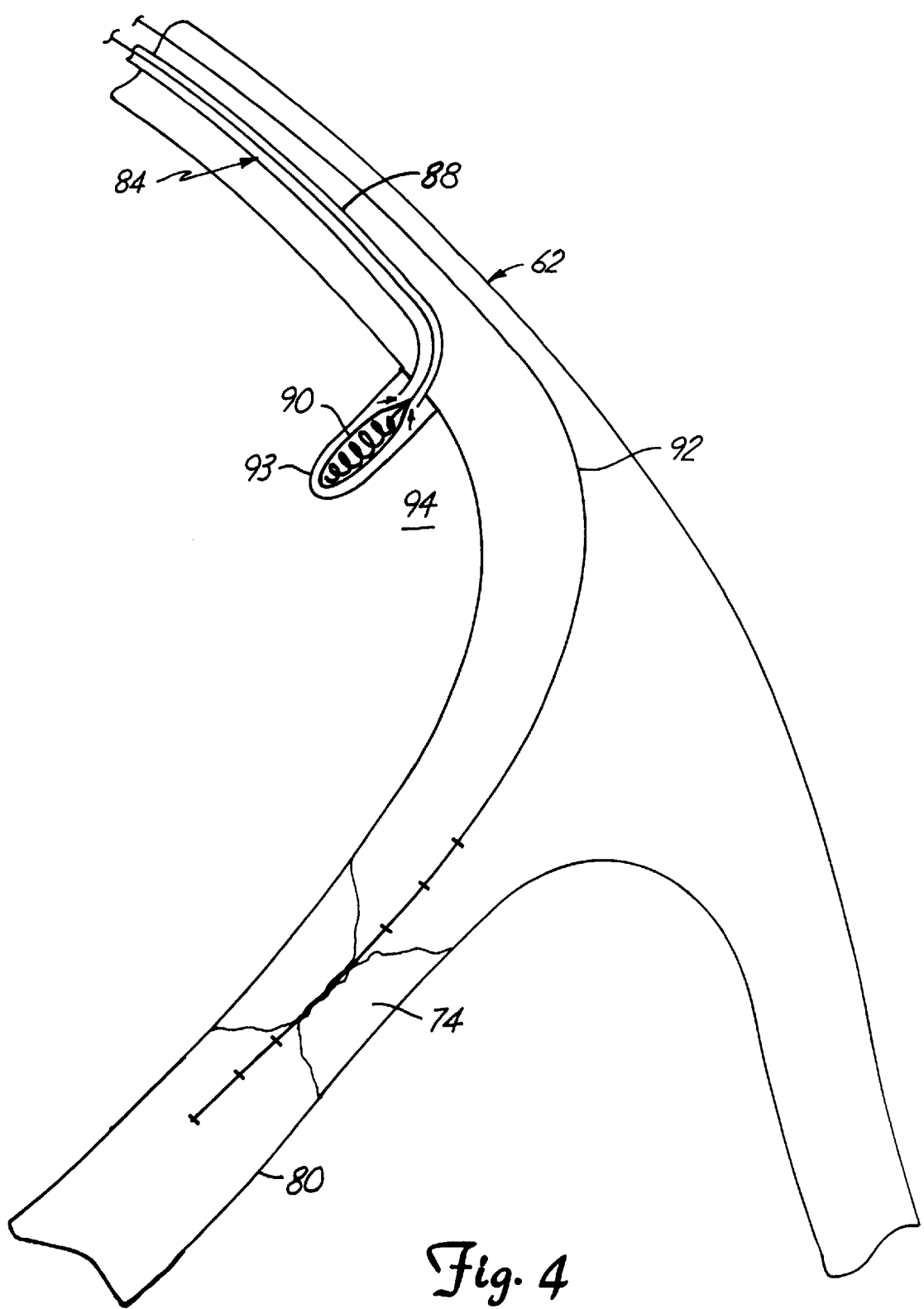

FIG. 4 illustrates additional steps used in performing a bypass in accordance with one embodiment of the present invention. For the sake of clarity, FIG. 4 is a greatly enlarged view of vessel 62 and branch 80.

In the embodiment shown in FIG. 4, restriction 74 is crossed with a conductive wire or fiber 92. Either the conductive wire or fiber 92 residing in the area of branch 80 distal of restriction 74, or cutting device 84, are provided with a transmitter, and the other (either the wire or fiber 92 which has been used to cross restriction 74 or cutting device 84) is provided with a receiver or sensor. In one preferred embodiment, the transmitter includes an array of active transmitters comprising one of ultrasound transmitters, radio frequency transmitters, a plurality of point light sources, or a single intense point light source, or an electromagnetic transmitter (such as where current is actively applied to a coil to induce a magnetic field thereabout). The receiver, or sensor, is a suitable device which is compatible with a transmitter so that it can receive or sense the signals provided by the transmitter.

For instance, when the transmitter includes an inductive magnetic coil, the receiver includes a magnetic sensor array to receive the signals induced in the coil. When the transmitter includes an ultrasound transmitter, the receiver includes an ultrasound imager so that the relative positioning of the receiver device and the transmitter can be determined. When the transmitter includes a single point light source, or an array of point light sources, the receiver or sensor includes a photodiode array or an imaging fiber optic bundle which can detect the light emitted by the light sources. In addition, when the transmitter includes an RF transmitter, the receiver includes a bidirectional antenna. Cutting member 90 of cutting device 84 is also preferably formed of radio-opaque material or has radio-opaque markings thereon. Therefore, when restriction 74 is not a total occlusion, contrast fluid can be injected through branch 80 to locate restriction 74. The relative position of restriction 74 and cutting device 84 can then be observed. In another preferred embodiment, radio-opaque markers are placed on the distal end of wire or fiber 92. Bi-plane fluoroscopy is then used to perform three dimensional visualization of the markers in branch 80 of artery 62 and cutting member 90 to bring them toward one another.

In another preferred embodiment, location of various items within the vasculature is accomplished using a triangulation and coordinate mapping system. In that embodiment, a radio frequency (RF) emitter is placed in the heart, or in the vasculature near the heart. The RF emitter is preferably placed on a catheter or another device, the placement of which must be guided. A number of reference electrodes (or receivers) are placed on the outside of the body at various points on the chest and back. In the preferred embodiment, three reference receivers are placed on the exterior of the body, two on the chest on opposite sides of the heart and one on the back. The three receivers are used to triangulate on the RF transmitter located on the device within the vasculature. Three dimensional modeling can be used, along with known motion analysis techniques to determine the placement and motion of the RF transmitter within the vasculature. Such a system can be used to obtain true position and the relative positions of different objects in the vasculature. Of course, a higher frequency signal could also be used, and a similar device could be used in which magnetic sensing devices are employed.

In any of the above cases, or similar cases, the relative position between the transmitter and receiver can be determined so that cutting member 90 cutting device 84 is properly located relative to the region of branch 80 distal of restriction 74.

FIG. 4 illustrates that cutting device 90 has pierced through the wall of vessel 62 and formed an aperture therein, and has begun to debulk (or form a channel 93 in) heart tissue 94 proximate the aperture which has been formed in the wall of vessel 62. In a preferred embodiment, aspiration is provided during the cutting or debulking operation to remove severed heart tissue pieces. Such aspiration is preferably accompanied by saline infusate to flush the area around cutting member 90. Aspiration can be provided using any suitable known technique, such as an aspiration catheter.

Figure 5:
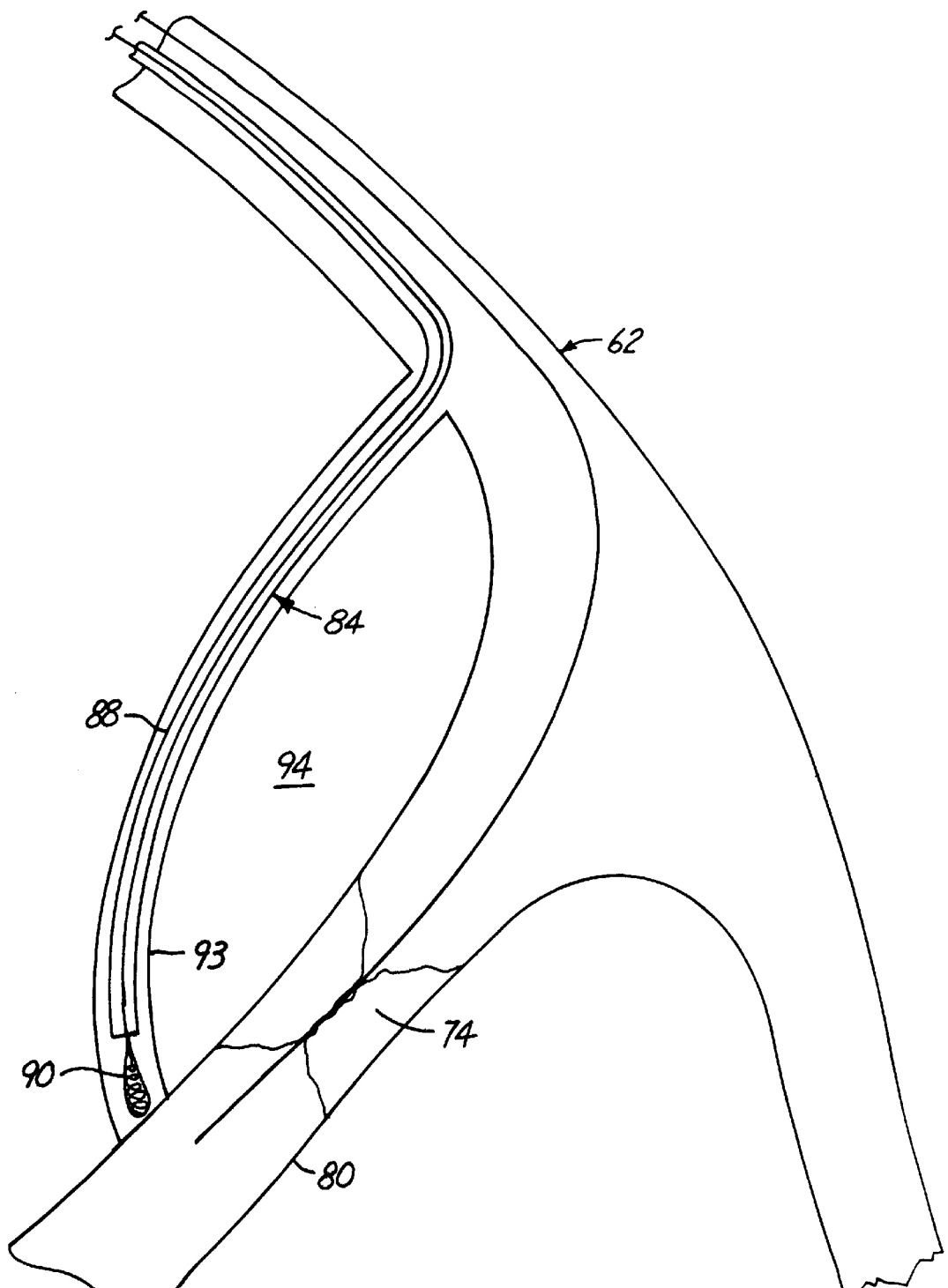

FIG. 5 illustrates another step in accordance with one aspect of one preferred embodiment of the present invention. In FIG. 5, cutting or debulking device 90 has been advanced to a region adjacent branch 80 distal of restriction 74. Cutting head 90 is then used to form an aperture in the wall of branch 80 at that location. FIG. 5 also illustrates that, in moving from the aperture in vessel 62 proximal of restriction 74, to the location shown in FIG. 5 (just distal of restriction 74) cutting or debulking head 90 has formed open channel (or trench) 93 in the surface of heart tissue 94 throughout that entire distance.

Figure 6:
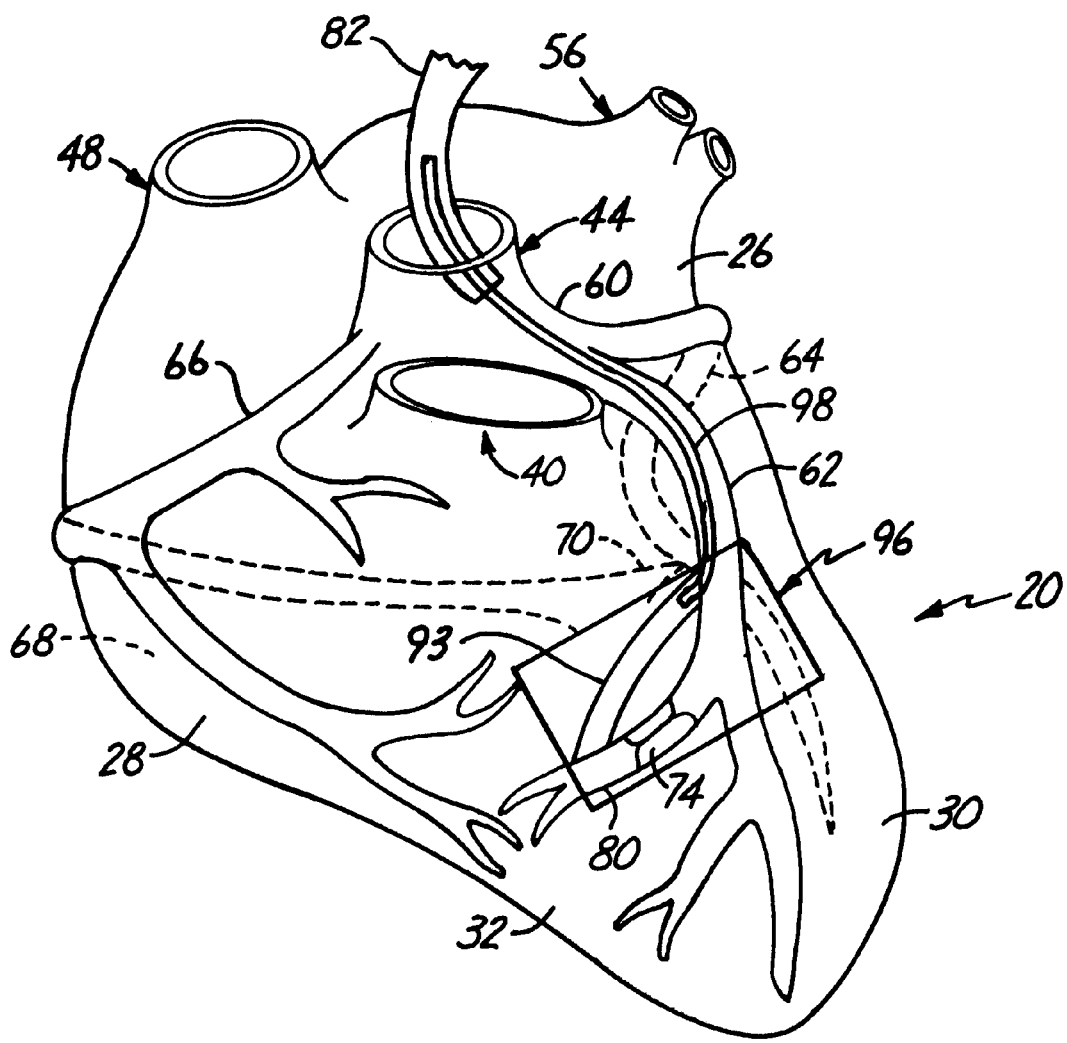

FIG. 6 illustrates additional steps in performing a bypass in accordance with one embodiment of the present invention. FIG. 6 illustrates trench 93 formed between an aperture in vessel 62 proximal of restriction 74, and extending to an aperture in branch vessel 80 distal of restriction 74. FIG. 6 also illustrates that patch 96 has been deployed over the entire length of channel 93. Patch 96 acts as a cover to channel 93 closing channel 93 to form a conduit between the aperture in vessel 62 proximal of restriction 74 and the aperture in vessel 80 distal of restriction 74. This provides a conduit for blood to flow around restriction 74.

Patch 96 is preferably formed of a biologically compatible material, and maybe a material which can act as a substrate for endothelialization. Suitable materials for patch 96 include poly(l-lactide) (PLLA), poly(D,L-lactide) (PLA), poly(glcolide) (PGA), poly(L-lactide-co-D.L. Lactide) (PLLA/PLA), poly(L-lactide-co-glycolide) (PLA/PGA), poly(glocolide-co-trimethylene carbonate) (PGA/PTMC), polydioxanone (PDS), polycaprolactone(PCL), polyhydroxybutyrate (PHBT), poly(phospazene), poly(D,L-lactide-co-caprolactone) (PLA/PCL), poly(glycolide-co-caprolactone) (PGA/PCL), poly(phosphase ester) and polyanhydrides. Other materials suitable for mixing with growth factors include hydrogels, polyethylene oxide and its copolymers, polyvinylpyrolidone, polyacrylates, polyesters, gelatins, collagens, proteins, sodium alginate, karaya gum, guar gum, agar, algin, carrageenans, pectins, xanthan, starch based gums, hydroxyalkyl and ethyl ethers of cellulose, sodium carboxymethyl cellulose, polyvinyl alcohol, and hydrophilic polyurethanes. In any case, once deployed, a suitable adhesive is preferably injected beneath patch 96 (between patch 96 and the biological tissues thereunder) to connect patch 96 to the biological tissue thereunder so that it covers channel 93 and thus forms the above-described conduit.

Suitable adhesives are preferably bioadhesives such as fibrin glues commercially available under the tradenames Tisseel or Tissucol from Immuno, Ag of Vienna, Austria; cyanoacrylates commercially available under the tradenames Histoacryl, Bucrylate, or Hexacryl; or Gelatin-Rocorcinol, formaldehyde, or mussel adhesive protein.

A variety of other adhesives are suitable for the present invention, both for adhering a patch over a heart wound, and for retaining angiogenic material within a wound. One adhesive is a hydrogel composed of gelatin and poly(L-glutamic acid)(PLGA). The hydrogel is formed by chemically cross linking gelatin and poly(L-glutamic acid). Another adhesive is fibrin glue. One suitable fibrin glue includes fibrinogen, thrombin, calcium chloride and factor VIII. Another family of adhesives is cyanoacrylates. Preferred cyanoacrylates include butyl-2-cyanoacrylate) Histoacryl), ethyl-2-cyanoacrylate, and octyl-2- cyanoacrylate. Gelatin-resorcinol formaldehydeglutaraldehyde is another suitable adhesive.

Applicants believe many polymers having suitable adhesive properties can also be utilized, including without limitation: polyurethanes having amino groups, di- and tri-functional diols; polyvinyl acetates; polyamides; polyvinyl alcohols; polystyrenes; polylactides; polyactones; block co-polymers including polyesters, polyamides, and polyurethanes; and combinations and mixtures thereof.

FIG. 6 also illustrates that cutting device 84 has been removed from the vasculature through guide catheter 82. Drug delivery device 98 has been advanced through guide catheter 82, and into the conduit formed by channel 93. Drug delivery device 98 is preferably any suitable known drug delivery device, such as a microcatheter, a perforated balloon delivery device, or any other suitable device. In the preferred embodiment, drug delivery device 98 is used to deliver a drug to the lumen of the conduit formed by channel 93 and patch 96 to enhance endothelial development in the lumen. In one preferred embodiment, the substance delivered by delivery device 98 includes a growth factor which enhances the growth of endothelial cells on the walls of the lumen. In another preferred embodiment, the substance delivered to the lumen with delivery device 98 includes endothelial cells which enhance endothelialization in the lumen.

Figure 7:
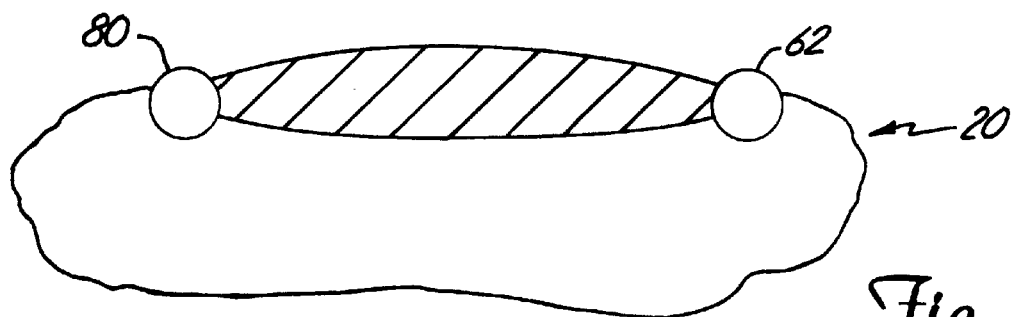
FIG. 7 is an enlarged partial cross-sectional view of a portion of the heart shown in FIGS. 1–6.

FIG. 7 is a greatly enlarged sectional view of heart 20 illustrating vessels 62 and 80 and the heart tissue lying therebetween. The cross-hatched portion shown in FIG. 7 is the heart tissue which is removed to form channel 93.

Figure 8:
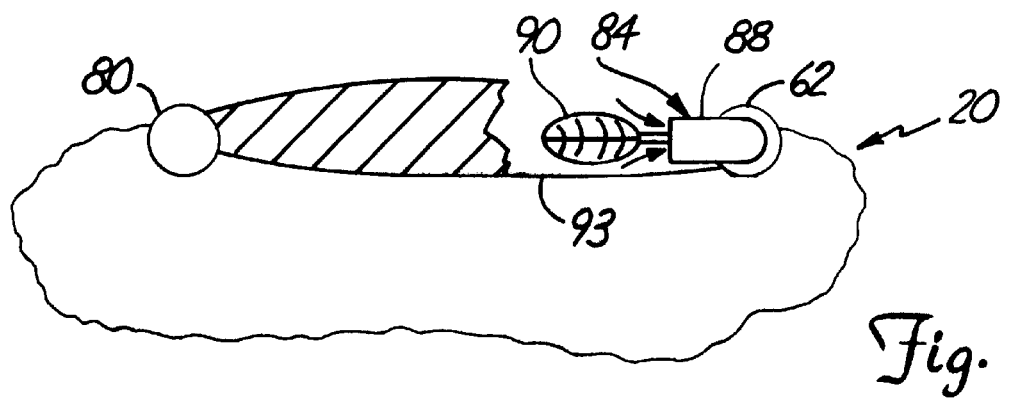
FIG. 8 illustrates the cross-section of FIG. 7 with a debulking device forming a channel in the heart tissue.

FIG. 8 illustrates the cross section shown in FIG. 7, with cutting or debulking device 84 having exited vessel 62 and advancing towards vessel 80 through the heart tissue. FIG. 8 illustrates that cutting head 90 forms open channel 93 by removing heart tissue from the surface of heart 20. FIG. 8 also illustrates the preferred embodiment in which the heart tissue pieces are aspirated through catheter 88, or another suitable aspiration device.

Vascular tissue is formed of a plurality of layers including the internal elastic lamina (IEL), the media, the adventicia, and myocardium. Heart tissue is formed of a plurality of layers including epicardium, myocardium and endocardium. In the preferred embodiment, channel 93 is formed by removing a portion of the layers. However, it should be noted that channel 93 can be formed by removing only one or more of the layers of heart tissue.

Figure 9:
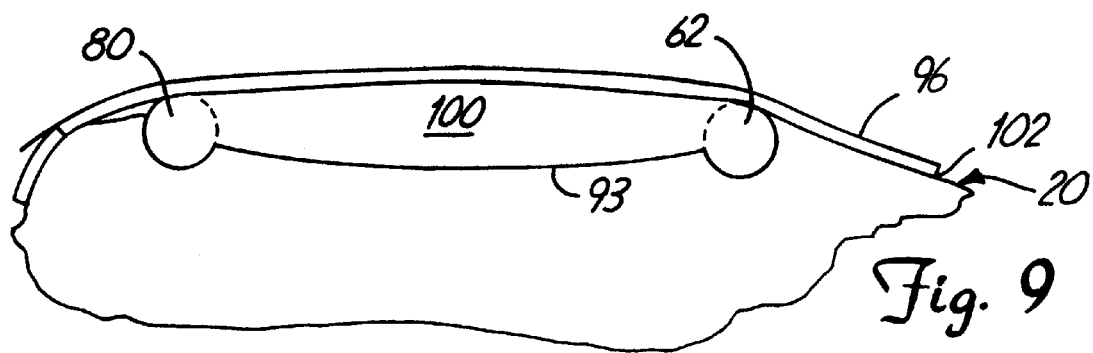
FIG. 9 illustrates a covering layer deployed over the channel formed as shown in FIG. 8.

FIG. 9 illustrates channel 93 after being covered by patch 96. In the preferred embodiment, patch 96 is deployed over channel 93, so that a conduit 100 is formed by the floor and sides of channel 93, and by patch 96. A suitable adhesive 102 is injected about the entire periphery of patch 96 between patch 96 and biological tissue thereunder (such as the tissue of heart 20). Adhesive 102 preferably acts to hold patch 96 closely adjacent channel 93 to substantially confine blood flow to the region between channel 93 and patch 96.

FIGS. 10A–10I illustrate a system 110 for deploying a patch 126, similar to patch 96. In the preferred embodiment, deployment system 110 includes containment sheath, or catheter 112, inner delivery sheath 114 (which includes a proximal section 116 and a distal, delivery end 118), deployment control shaft 120 (which includes a proximal deployment member 122 which is attached to control shaft 120), distal positioning end 124, and rolled patch 126.

In the preferred embodiment deployment control shaft 120 and proximal deployment member 122 are connected to one another, and are movable within sheath 114. Distal positioning segment 124 is formed suitably to position the distal end of control shaft 120 at a desired location in the body. Sheath 114 is movable within catheter 112, and has rolled patch 126 located in a distal end 118 thereof.

FIG. 10B is a cross-sectional view taken along section lines 10B—10B of FIG. 10A. FIG. 10B shows that, in one preferred embodiment, patch 126 is attached to, and rolled about or coiled about deployment control shaft 120 within catheters 112 and 114. FIG. 10C illustrates a second preferred embodiment, in which patch 126 is simply formed into a resilient C-shape within catheters 112 and 114. In the embodiment shown in FIG. 10C, patch 126 can optionally be connected to deployment control shaft 120, or can simply be independently coiled within shaft 114.

In either of the above embodiments, distal end 124 of system 110 is advanced to a site in the body in which it overlies one or both of vessels 62 and 80, and adjacent heart tissue. Then, control wire 120, proximal positioning member 122 and sheath 114 are advanced out of the distal end of catheter 112. Sheath 114 is then withdrawn to expose coiled patch 126. Deployment control shaft 120 is then rotated so that coiled patch 126 is unrolled to lie substantially flat on the heart tissue. Suitable portions of the entire system 110 are then manipulated, if necessary, such that the unrolled patch 126 is in the desired location. Finally, the connection between deployment control shaft 120 and coil patch 126 is severed and the patch is suitably located such that it covers channel 93 and the adjacent heart tissue.

In the embodiment shown in FIG. 10C, where patch 126 is not coupled to deployment control shaft 120, sheath 114 is simply withdrawn from the outer periphery of patch 126, and patch 126 is biased to deploying outwardly in a flat position adjacent the heart tissue.

In another preferred embodiment, rotation of shaft 120 is not necessary for deployment of patch 126. Instead, patch 126 is formed with nitinol wires or ribs therein which are biased to a flat position. Being coiled or curved within shaft 114 as shown in FIGS. 10B and 10C, the patch 126 exerts a spring force on the inside of sheath 114. When sheath 114 is withdrawn from patch 126, the spring force in patch 126 causes it to flatten out and lie over the desired heart tissue.

Figure 10E:
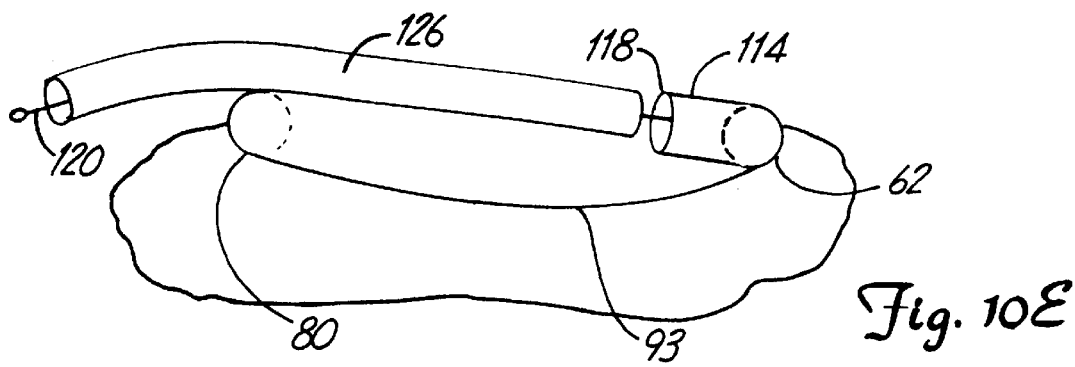
Figure 10F:
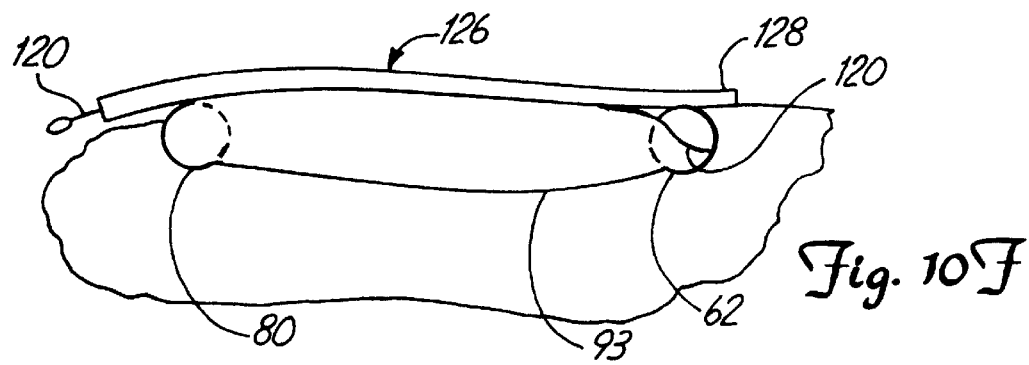
Figure 10G:
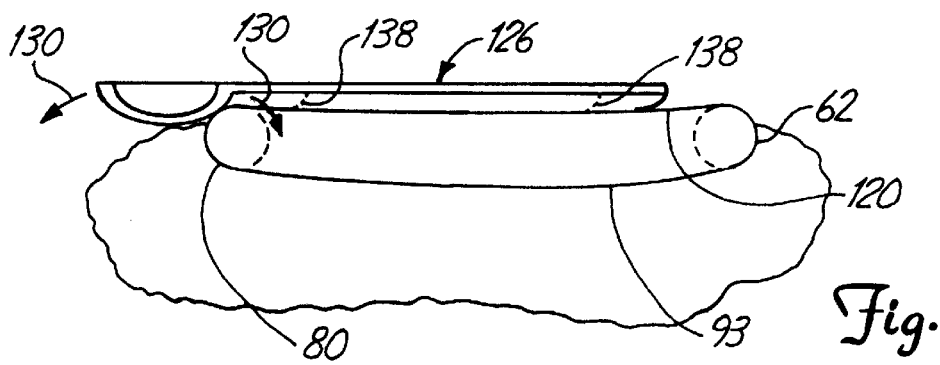
Figure 10H:
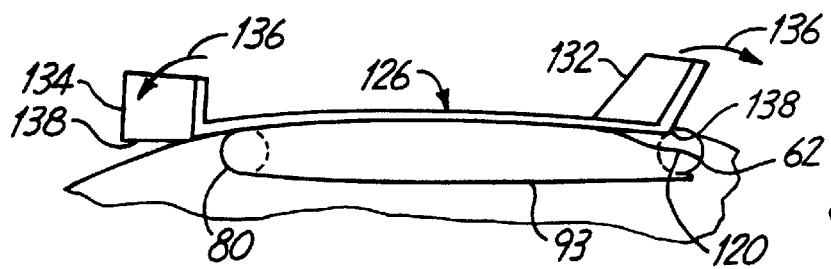
Figure 10I:
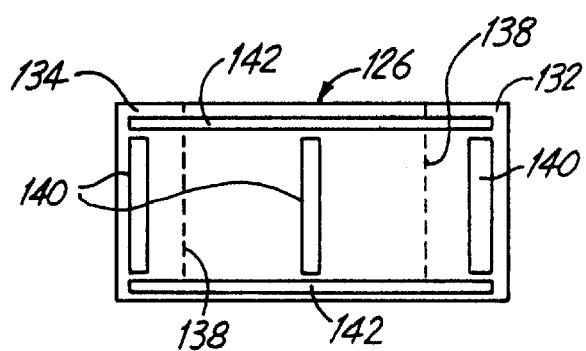

As discussed in greater detail with respect to FIG. 10I, the nitinol wires are preferably embedded in the outer edges of patch 126. In one preferred embodiment, the shape memory properties of nitinol are used, and they are activated at body temperatures such that, as patch 126 warms, it assumes its predetermined shape memory position. In another preferred embodiment, the super elastic properties of nitinol are used to cause patch 126 to assume the desired position.

Deployment of patch 126 is illustrated in greater detail, in accordance with one embodiment of the present invention, in FIGS. 10D–10F. FIG. 10D illustrates that channel 93 has already been formed in the heart tissue between vessels 62 and 80. FIG. 10D also illustrates that catheter 112 has been advanced to a position in which it overlies vessel 80 and a portion of the heart tissue distal of vessel 80. FIG. 10D also illustrates that internal sheath 114 has been advanced from within catheter 112 by a length. FIG. 10D further illustrates that a portion of coiled patch 126 has also been advanced out through the distal end 118 of sheath 114 (or sheath 114 has been withdrawn to expose a portion of patch 126).

FIG. 10E illustrates that internal sheath 114 has been withdrawn to expose substantially the entire outer periphery of coiled patch 126. In one preferred embodiment, upon exposure to body temperature, coiled patch 126 uncoils and expands in a substantially flat configuration above channel 93 between vessels 62 and 80. In another preferred embodiment, deployment control shaft 120 is rotated to unroll or uncoil coiled shaft 126. In either embodiment, patch 126 eventually resides in a substantially flat configuration which overlies channel 93.

Then, deployment control shaft 120 is preferably manipulated (as shown better in FIG. 10F) to cause a distal end 128 of patch 126 to be withdrawn to a position such that it covers channel 93 and vessel 62. Patch 126 is then secured to the heart tissue and the connection between shaft 120 and patch 126 is severed. Of course, the connection between shaft 120 and patch 126 can be severed prior to connecting patch 126 to the heart tissue, whichever is preferred by the particular user.

In order to sever the attachment between shaft 120 and patch 126, any suitable severing system can be used. Such severing systems include the mechanical actuation of a suitable release mechanism, cutting the attachment with a separate or integrated blade, or using RF energy to burn the attachments to thereby sever shaft 120 from patch 126.

Patch 126 can be suitably attached to the surface of the heart using adhesives which are activated upon contact with the heart surface. Some such adhesives include moisture activated adhesives. Alternatively, patch 126 can be attached to the heart tissue with cyanoacrylate applied to the surface of the heart tissue just prior to deployment of patch 126 thereon. Such application of cyanoacrylate, or another suitable adhesive, can be accomplished through a delivery catheter, or another suitable device.

In yet another alternative, a two-part adhesive or fixating system can be used. In such a system, a first component or chemical is applied liberally to the heart surface. The second component of the fixating system is attached to the patch. In this way, when the surface of the patch comes into contact with the surface of the heart, a bond is formed. Materials such as fibrin based adhesives, or other biocompatible adhesive systems can be used in order to implement such an embodiment.

FIGS. 10G and 10H illustrate yet another preferred embodiment in deploying patch 126. In FIGS. 10G and 10H, patch 126 is folded or coiled in two directions. First, patch 126 is folded or coiled in the axial direction as indicated by FIGS. 10B or 10C. In addition, patch 126 is folded in the longitudinal direction, preferably at one or more fold lines on the longitudinal ends of patch 126.

FIG. 10G illustrates patch 126 after initially being deployed over channel 93. Patch 126 is shown uncoiling or folding outwardly in the first, axial direction as generally indicated by arrows 130. Position control shaft 120 is used to control the position of patch 126, and patch 126 again folds outwardly in a second, longitudinal direction, as indicated by FIG. 10H. FIG. 10H shows that longitudinally extreme flaps 132 and 134 fold outwardly generally in the directions indicated by arrows 136 about fold lines 138. In this way, patch 126 is fully deployed over channel 93, and vessels 62 and 80, without the need for substantial and cumbersome repositioning of patch 126 relative to the vasculature. Again, patch 126 is attached to the heart tissue in a similar manner as described above, and the connection between shaft 120 and patch 126, if such a connection is used, is severed to leave patch 126 in place.

FIG. 10I illustrates one preferred embodiment of patch 126. Patch 126 is formed of a suitable biocompatible material having a plurality of nitinol ribs or wires which are embedded in patch 126, or connected thereto. In one preferred embodiment, a plurality of axially directed nitinol wires 140 are disposed at intervals along the longitudinal axis of patch 126. In addition, longitudinally directed nitinol ribs or wires 142 are also disposed on patch 126. The axially directed ribs 140 facilitate the folding outward or uncoiling of patch 126 in the axial direction, while the longitudinally directed ribs or wires 142 facilitate the folding outward of the flaps 132 and 134 of patch 126 along fold lines 138.

Figure 10J:
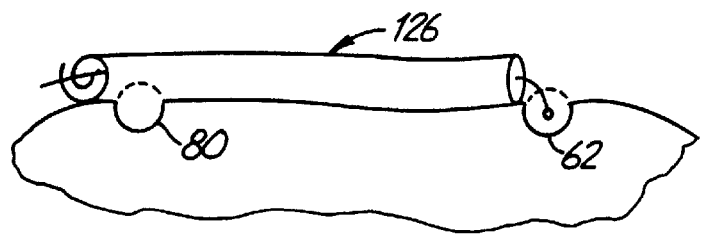
Figure 10K:
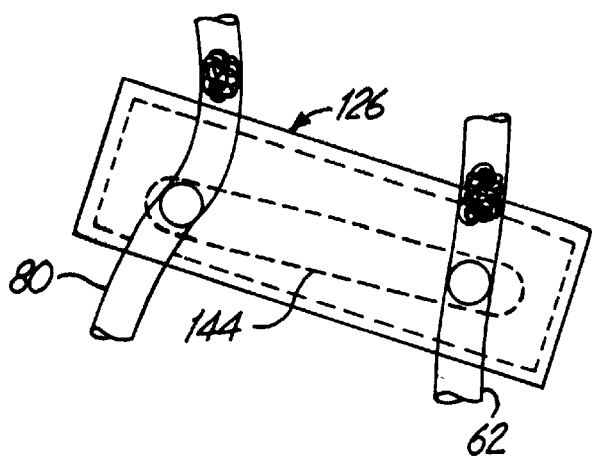

FIGS. 10J and 10K illustrate another aspect of the preferred embodiment in which patch 126 is used, without forming channel 93. FIG. 10J illustrates coiled patch 126 which has been disposed over vessels 62 and 80. Rather than forming a channel in the heart tissue, a cutting device, such as that shown in FIG. 5, is simply used to perforate vessel 62. The cutting device is then advanced to vessel 80 and is used to pierce vessel 80 as well. Alternatively, vessel 80 can be pierced from within. After the apertures are formed in vessels 62 and 80, patch 126 is deployed over the apertures formed in vessels 62 and 80, and over the heart tissue, as described above.

FIG. 10K illustrates patch 126 in the deployed position. FIG. 10K also illustrates that vessel 80 is the occluded vessel, and patch 126 is placed over the apertures in vessels 62 and 80. One preferred connection pattern is also illustrated in FIG. 10K. The dashed lines in FIG. 10K illustrate, for example, the application area of adhesive, or the connection area between patch 126 and the heart tissue and vessels 62 and 80. In the preferred embodiment, patch 126 is connected to the heart in any or all areas, other than an inner boundary illustrated by dashed line 144. In this way, adhesive can be applied to the remainder of the patch and the heart tissue under that portion of the patch, while leaving the patch and the heart tissue under the patch in the area bounded by dashed line 144 free of adhesive. The area under patch 126 in the area bounded by dashed line 144 thus forms a conduit between the aperture in vessels 62 and the aperture in vessel 80. By simply not connecting patch 126 in this area, blood flow can be conducted between vessels 62 and 80 through that conduit. This saves the time and manipulation required to form channel 93.

Figure 11:
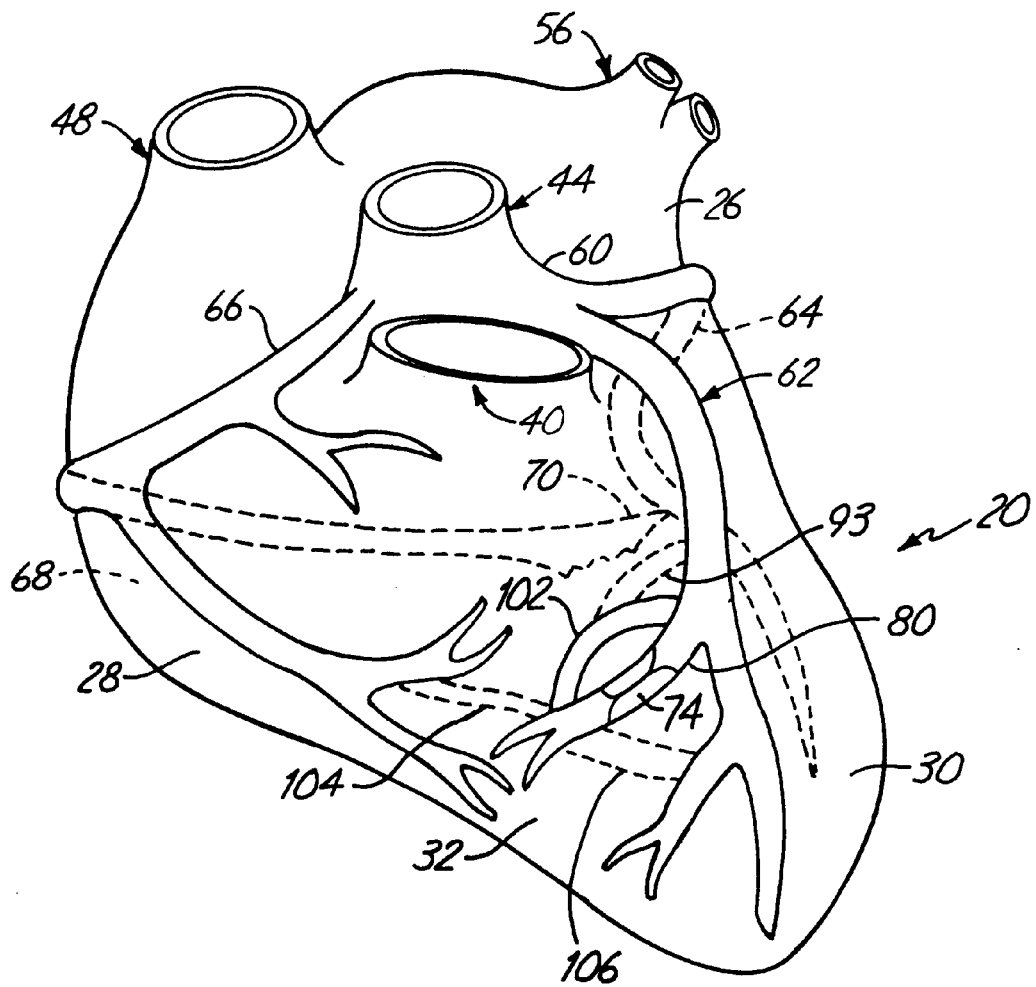
FIG. 11 illustrates alternative embodiments of performing a bypass in accordance with the present invention.

FIG. 11 illustrates a plurality of different embodiments in accordance with the present invention. FIG. 11 illustrates channel 93 which has been described above. However, it should also be noted that additional channels can be formed between additional points of the vasculature and branch 80 distal of restriction 74. For instance, FIG. 11 illustrates channel 102 which has been formed with both apertures in branch 80. In other words, the cutting device was advanced all way down into branch 80 and then was used to cut an aperture in the wall of branch 80 and simply form a channel around restriction 74 and rejoin branch 80 distal of restriction 74.

FIG. 11 also illustrates two other embodiments in which channels 104 or 106 are formed. Channel 104 is formed between the region of vessel 80 distal of occlusion 74 and a completely different supply vessel, such as a branch of right main coronary artery 66. In that preferred embodiment, blood flow through artery 66 is preferably temporarily occluded while the aperture is formed in the branch of artery 66 and while the channel 104 is formed.

Similarly, channel 106 is shown in FIG. 11 extending between the region of branch 80 distal of restriction 74, and another supply vessel which is another branching vessel, branching off of artery 62.

In all of the above instances, where the supply vessel is either a neighboring vessel or the restricted vessel itself, patch 96 is appropriately placed above the respective channel to form the necessary conduit between the supply vessel and the region of branch 80 distal of restriction 74.

It should also be noted that the present invention has been described with respect to stopping blood flow through the relevant vessels using occlusion balloons. Occlusion balloons have a fairly low instance of emboli formation, and therefore have a fairly low instance of neurological problems which result from formation of emboli. However, other systems can be employed for temporarily occluding blood flow through the vessels, or for temporarily stopping blood flow through the relevant vasculature, through any other suitable means.

Although the present invention has been described with reference to preferred embodiments, workers skilled in the art will recognize that changes may be made in form and detail without departing from the spirit and scope of the invention.

What is claimed is:

1. A method of bypassing a restriction in a restricted vessel, the restricted vessel lying closely proximate heart tissue, the method comprising:

forming an aperture in a supply vessel suitable for providing a blood supply;

forming an aperture in the restricted vessel distal of the restriction in the restricted vessel;

removing heart tissue from the surface of the heart to form a channel in the surface of the heart tissue between the aperture in the supply vessel and the aperture in the restricted vessel distal of the restriction; and covering the channel to form a conduit to conduct blood from the supply vessel to the restricted vessel distal of the restriction.

2. The method of claim 1 wherein forming an aperture in a supply vessel, comprises:

forming the aperture in a region of the restricted vessel proximal of the restriction.

3. The method of claim 1 wherein the supply vessel comprises a neighboring vessel residing proximate the restricted vessel and wherein forming an aperture in a supply vessel, comprises:

forming an aperture in the neighboring vessel proximate the restricted vessel.

4. The method of claim 3 wherein the neighboring vessel comprises a parent vessel of the restricted vessel, and wherein forming an aperture in the neighboring vessel, comprises:

forming an aperture in the parent vessel proximate the restricted vessel.

5. The method of claim 3 wherein the neighboring vessel comprises a branching vessel branching from a region of the restricted vessel proximal of the restriction, and wherein forming an aperture in the neighboring vessel, comprises:

forming an aperture in the branching vessel proximate the restricted vessel.

6. The method of claim 1 wherein covering the channel comprises:

applying a patch over the channel.

7. The method of claim 6 wherein applying a patch comprises:

adhering the patch to heart tissue proximate the channel.

8. The method of claim 6 wherein applying a patch comprises:

delivering the patch, intravascularly, in a first configuration;

deploying the patch into a second configuration, larger than the first configuration, to cover the channel; and connecting the patch to heart tissue to form the conduit.

9. The method of claim 8 wherein deploying the patch includes allowing the patch to assume the second configuration under the influence of a superelastic material.

10. The method of claim 8 wherein deploying the patch comprises:

expanding the patch in axial and longitudinal directions relative to the first configuration.

11. The method of claim 8 wherein deploying the patch comprises:

unrolling the patch from a coiled configuration to an expanded, uncoiled configuration.

12. The method of claim 1 and further comprising:

delivering a substance to the channel to enhance endothelialization of the heart tissue.

13. The method of claim 12 wherein delivering a substance comprises:

accessing the channel with a catheter; and injecting, through the catheter, the substance.

14. The method of claim 12 wherein delivering a substance comprises:

delivering endothelial cells to the channel.

15. The method of claim 12 wherein delivering a substance comprises:

delivering a growth factor to the channel.

16. The method of claim 1 wherein covering the channel comprises:

delivering the patch, intravascularly, in a first configuration;

allowing the patch to assume a second configuration, larger than the first configuration, under the influence of a shape memory material; and connecting the patch to heart tissue to form the conduit.

17. A method of bypassing a restriction in a restricted vessel, the method comprising:

accessing a region in a supply vessel proximate the restricted vessel and closely proximate heart tissue and suitable for providing a blood supply;

forming an aperture in the supply vessel;

accessing a region of the restricted vessel closely proximate heart tissue and distal of the restriction;

forming an aperture in the restricted vessel distal of the restriction;

creating a channel in heart tissue between the aperture in the supply vessel and the aperture in the restricted vessel; and covering the channel to form a conduit.

18. A method of bypassing a restriction in a restricted coronary artery, the method comprising:

forming an aperture in a supply coronary artery proximate the restricted coronary artery;

forming an aperture in the restricted coronary artery distal of the restriction;

removing heart tissue from the surface of the heart to form a channel in the surface of the heart tissue between the aperture in the supply coronary artery and the aperture in the restricted coronary artery distal of the restriction; and covering the channel to form a conduit to conduct blood from the supply coronary artery to the restricted coronary artery distal of the restriction.

19. The method of claim 18 wherein forming an aperture in the supply coronary artery, comprises:

forming the aperture in a region of the restricted coronary artery proximal of the restriction.

20. The method of claim 18 wherein the supply coronary artery comprises a neighboring coronary artery residing proximate the restricted vessel and wherein forming an aperture in the supply coronary artery, comprises:

forming an aperture in the neighboring coronary artery proximate the restricted coronary artery.

21. The method of claim 18 wherein covering the channel comprises:

applying a patch over the channel.

22. The method of claim 21 wherein applying a patch comprises:

adhering the patch to heart tissue proximate, the channel.

* * * * *

UNITED STATES PATENT AND TRADEMARK OFFICE
CERTIFICATE OF CORRECTION

PATENT NO.    : 6,213,126 B1  
DATED         : April 10, 2001  
INVENTOR(S)   : Daniel M. LaFontaine et al.

It is certified that error appears in the above-identified patent and that said Letters Patent is hereby corrected as shown below:

<u>Title page,</u>  
Item [56], References Cited insert the following:  
U.S. PATENT DOCUMENTS

| | | | |
|---|---|---|---|
| -- 5,836,311 | 11/1998 | Borst et al. | 128/897 |
| 5,849,036 | 12/1998 | Zarate | 623/1 |
| 5,855,210 | 01/1999 | Sterman et al. | 128/898 |
| 5,855,614 | 01/1999 | Stevens et al. | 623/11 |
| 5,868,770 | 02/1999 | Rygaard | 606/167 -- |

FOREIGN PATENT DOCUMENTS

| | | |
|---|---|---|
| -- WO 98/51223 | 11/1998 | (WO) |
| WO 98/52474 | 11/1998 | (WO) |
| WO 98/52475 | 11/1998 | (WO) |
| WO 98/57590 | 12/1998 | (WO) |
| WO 98/57591 | 12/1998 | (WO) |
| WO 98/57592 | 12/1998 | (WO) |
| WO 99/04845 | 02/1999 | (WO) -- |

Signed and Sealed this

Eleventh Day of June, 2002

*Attest:*

JAMES E. ROGAN  
*Attesting Officer*  
*Director of the United States Patent and Trademark Office*